United States Patent [19]

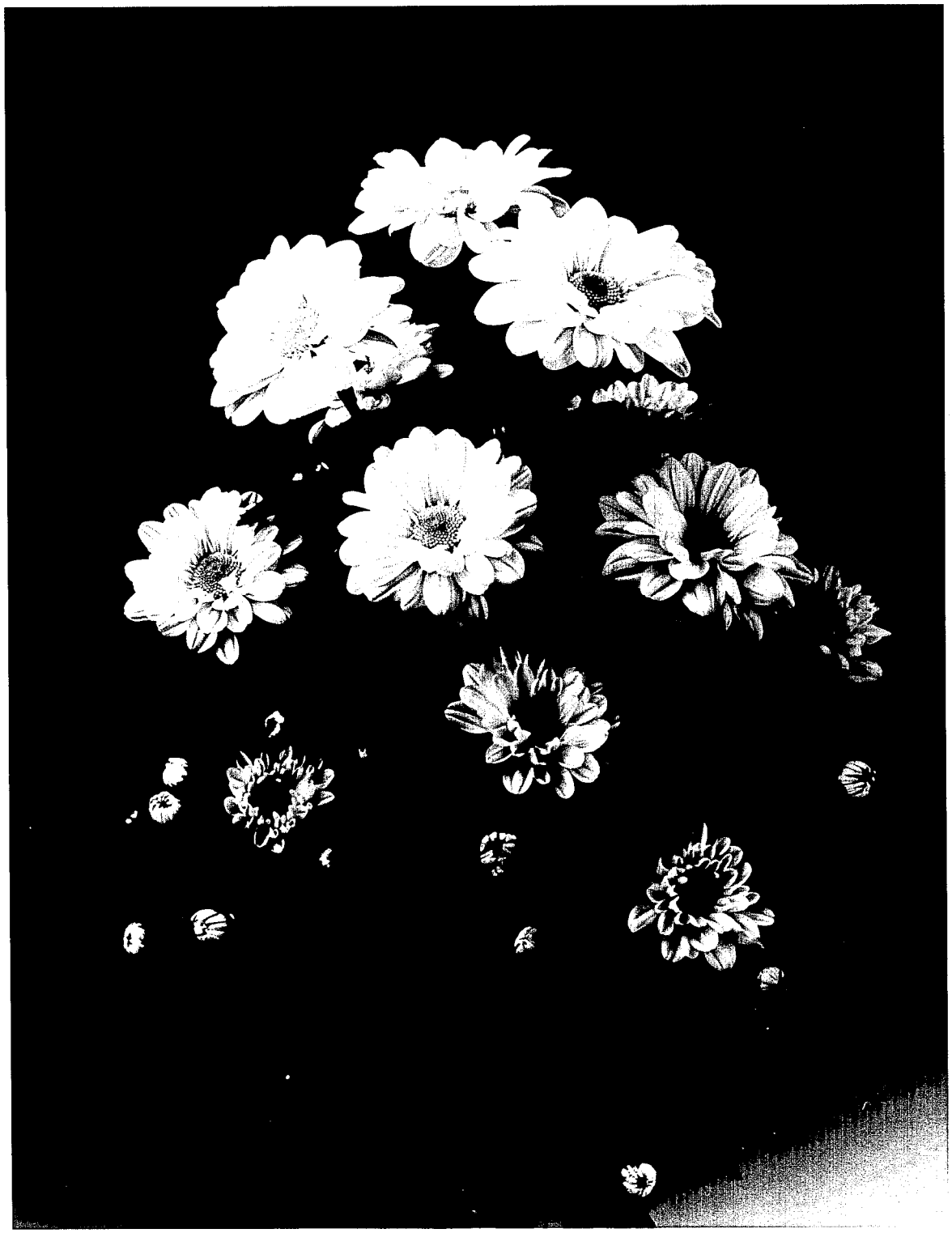

Van der Knaap

[11] Patent Number: Plant 6,734

[45] Date of Patent: Apr. 11, 1989

[54] CHRYSANTHEMUM PLANT NAMED SALMON IMPALA

[75] Inventor: Jacques C. M. Van der Knaap, De Lier, Netherlands

[73] Assignee: Fides Beheer B.V., De Lier, Netherlands

[21] Appl. No.: 123,901

[22] Filed: Nov. 23, 1987

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Salmon Impala, particularly characterized by its flat capitulum form; single daisy capitulum type; salmon pink ray floret color; diameter across the face of the capitulum of 45–75 mm; excellent growth habit, and its yellow-green to yellow disc florets.

1 Drawing Sheet

The present invention comprises a new and distinct cultivar of Chrysanthemum, botanically known as *Chrysanthemum morifolium,* and referred to by the cultivar name Salmon Impala.

Salmon Impala is a spontaneous mutation of Impala, disclosed in a pending application of applicant. The new cultivar was discovered by applicant in a cultivated bed of plants of the parent cultivar Impala in De Lier, Holland in 1984.

The first act of asexual reproduction of Salmon Impala was accomplished when vegetative cuttings were taken after discovery of the mutation in a controlled environment in De Lier, The Netherlands by a technician working under formulations established and supervised by Jacques C. M. Van der Knaap. Horticultural examination of selected units has demonstrated that the combination of characteristics as herein disclosed for Salmon Impala are firmly fixed and are retained through successive generations of asexual reproduction.

Salmon Impala has not been observed under all possible environmental conditions. The phenotype may vary significantly with variations in environment such as temperature, light intensity, and day length. The following observations, measurements and comparisons describe plants grown in De Lier, The Netherlands under greenhouse conditions which approximate those generally used in commercial practice.

The following traits have been repeatedly observed and are determined to be basic characteristics of Salmon Impala, which in combination distinguish this Chrysanthemum as a new and distinct cultivar:

1. Flat capitulum form.
2. Single, daisy capitulum type.
3. Salmon pink ray floret color.
4. Diameter across the face of the capitulum is 45–75 mm.
5. Yellow-green (immature) to yellow (mature) disc florets.
6. Excellent vigor and growth habit.

In comparison to Impala, Salmon Impala has a better growth habit, salmon pink ray florets, and a somewhat larger flower. The flower type, capitulum form, flower size, and disc floret color of Salmon Impala are similar to those same characteristics of Impala.

Salmon Impala is also similar in many respects except flower color to the cultivars Cream Impala, Pink Impala and Apricot Impala, all of which are mutations of Impala and disclosed in pending applications of applicant. However, Salmon Impala has better vigor, more flower production, and 2–3 days slower response than the mutations referred to.

The accompanying photographic drawing shows in side view typical inflorescence and foliage characteristics of Salmon Impala, with colors being as true as possible with illustrations of this type.

In the following description, color references are made to the Royal Horticultural Society Colour Chart. The color values were determined between 11:00 a.m. and 12:00 noon in August under natural daylight at De Lier, The Netherlands.

Classification:

*Botanical.*—*Chrysanthemum morifolium,* Ramat., cv. Salmon Impala.

*Commercial.*—Cut daisy spray.

INFLORESCENCE

A. Capitulum:
- *Form.*—Flat.
- *Type.*—Daisy.
- *Diameter across face.*—60–75 mm.

B. Corolla of ray florets:
- *Color (general tonality from a distance of three meters).*—Salmon pink.
- *Color (upper surface).*—RHS 56D.

C. Corolla of disc florets:
- *Color (mature).*—Yellow.
- *Color (immature).*—Yellow-green.

D. Reproductive organs:
- *Androecium.*—Present in disc florets; numerous.
- *Gynoecium.*—Present in both disc and ray florets; numerous.

PLANT

A. General appearance:
- *Height.*—90 cm.

B. Foliage:
- *Color (upper surface).*—RHS 147A.
- *Shape.*—Long lobed and deeply serrated.

I claim:

1. A new and distinct Chrysanthemum plant named Salmon Impala, as described and illustrated, and parts thereof.

* * * * *